United States Patent [19]
Colombo et al.

[11] Patent Number: 5,738,707
[45] Date of Patent: Apr. 14, 1998

[54] DEVICE AND METHOD FOR THE SEPARATION OF A SAMPLE INTO ITS INDIVIDUAL COMPONENTS IN A CAPILLARY CONDUIT OF A GAS CHROMATOGRAPHY ANALYSIS APPARATUS

[75] Inventors: Pier Albino Colombo, Treviglio; Paolo Magni, Besana In Brianza; Fausto Munari, Milan; Sorin Trestianu, Rodano, all of Italy

[73] Assignee: Thermoquest Italia S.p.A., Italy

[21] Appl. No.: 766,397

[22] Filed: Dec. 12, 1996

[30] Foreign Application Priority Data

Dec. 29, 1995 [IT] Italy ............... MI95A2785

[51] Int. Cl.$^6$ .......................... B01D 15/08
[52] U.S. Cl. .......... 95/15; 95/82; 95/87; 96/102
[58] Field of Search ............ 73/23.22, 23.25, 73/23.27, 23.29, 23.36; 95/15, 82, 87; 96/101–103

[56] References Cited

U.S. PATENT DOCUMENTS

| | | | |
|---|---|---|---|
| 4,805,441 | 2/1989 | Sides et al. | 95/87 X |
| 4,948,389 | 8/1990 | Klein et al. | 95/87 X |
| 4,976,750 | 12/1990 | Munari | 95/82 X |
| 4,994,096 | 2/1991 | Klein et al. | 95/15 |
| 5,083,450 | 1/1992 | Grindstaff | 73/23.25 |
| 5,096,471 | 3/1992 | Sacks et al. | 95/87 |
| 5,108,466 | 4/1992 | Klein et al. | 95/82 X |
| 5,305,232 | 4/1994 | Chimowitz et al. | 96/102 X |
| 5,405,432 | 4/1995 | Snyder et al. | 95/82 |
| 5,431,712 | 7/1995 | Henderson et al. | 95/82 X |
| 5,476,000 | 12/1995 | Henderson et al. | 95/15 X |
| 5,524,084 | 6/1996 | Wang et al. | 73/23.22 X |
| 5,545,252 | 8/1996 | Hinshaw et al. | 95/82 X |
| 5,567,227 | 10/1996 | Henderson | 95/82 X |

FOREIGN PATENT DOCUMENTS 63-131059 6/1988 Japan ............... 96/101

*Primary Examiner*—Robert Spitzer
*Attorney, Agent, or Firm*—Corbin Gittes & Samuel

[57] ABSTRACT

A device and method are described for the gas chromatographic separation of a sample, aimed in particular at the analysis of large volume samples. Provision is made for the use of calculating and memorizing a plurality of reference values corresponding to the evaporation rates of solvents combined with a carrier gas for a corresponding plurality of discrete values representing the conditions of pressure, temperature, injected sample volume and sample injection rate. The effective solvent evaporation rate is then calculated in correspondence to the effective conditions in which the process is carried out to determine the volumetric fraction of the sample which is transferred through the capillary column in relation to its characteristics and geometrical dimensions.

18 Claims, 5 Drawing Sheets

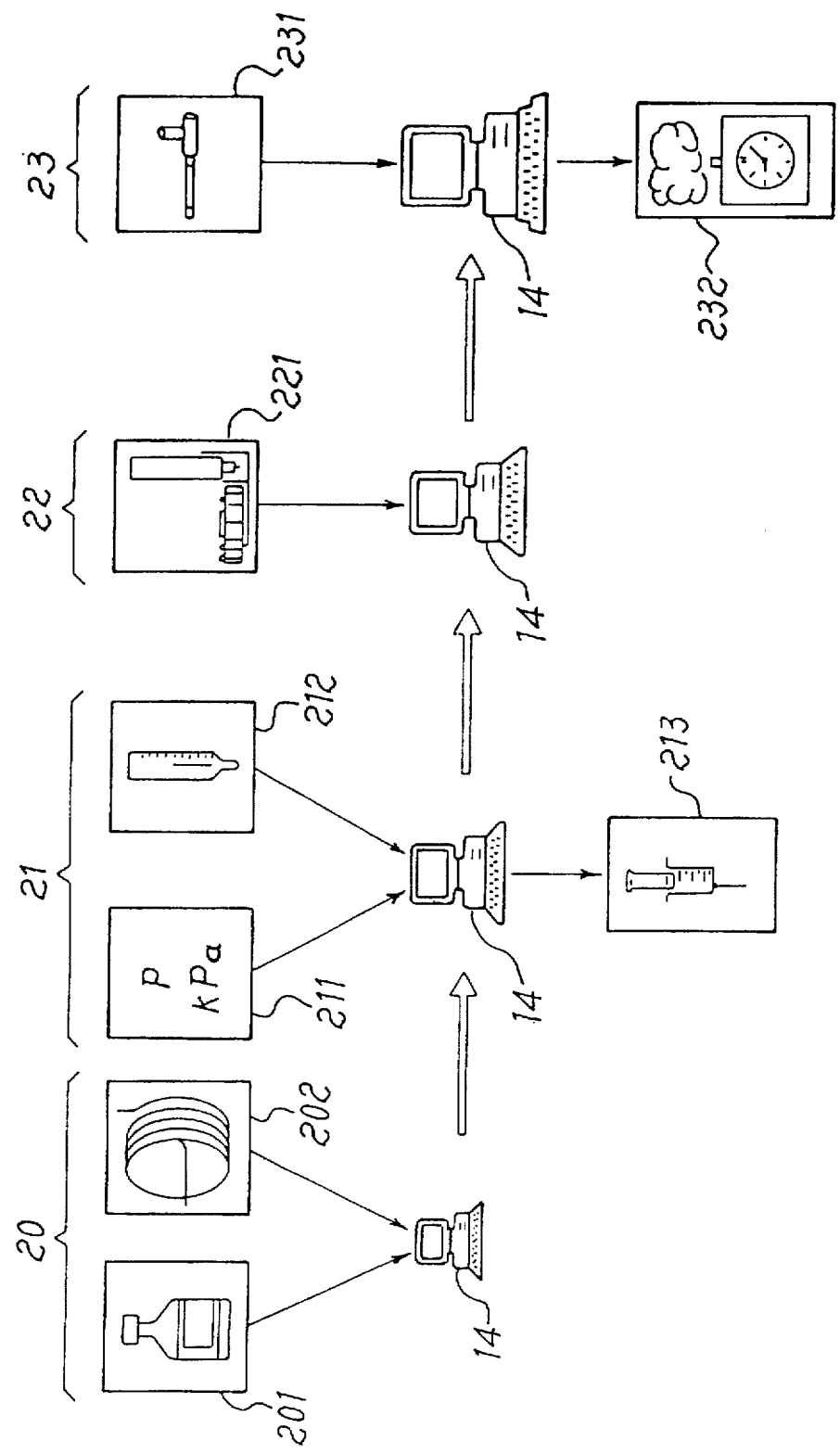

DEVICE AND METHOD FOR THE SEPARATION OF A SAMPLE INTO ITS INDIVIDUAL COMPONENTS IN A CAPILLARY CONDUIT OF A GAS CHROMATOGRAPHY ANALYSIS APPARATUS

BACKGROUND OF THE INVENTION

The present invention relates to a device and a method for the separation into its individual components of a sample which is injected into a stream of carrier gas in the capillary conduit of a gas chromatography analysis apparatus. "Sample" here means a certain quantity of a solution of one or more components dissolved in a solvent.

FIELD OF THE INVENTION

The invention has applications in gas chromatography analysis in general and in the gas chromatography analysis of high volume samples in particular.

It is known that, gas chromatography analysis involves a complex preparation method for the sample which includes such steps as extraction, concentration and purification. These operations are not only time consuming but also introduce a series of errors into the result of the analysis itself.

Gas chromatographic analysis is usually carried out on an apparatus fitted with a capillary conduit consisting generally of a pre-column "retention gap", a capillary analytical column lodged in an oven, and an injector upstream of the pre-column. There is a supply line connected to the injector for a carrier gas which carries the sample through the capillary conduit. Generally, a means of regulating the oven temperature and a means of regulating the pressure of the carrier gas fed into the injector are provided.

In particular, e.g. for an apparatus fitted with "on-column" type injectors, there is a "T" link between the pre-column and the capillary analytical column that connects the capillary conduits to a valve, known as "Solvent Vapour Exit" (SVE), by a length of capillary tubing. The SVE permits the vapour phase of the solvent to exhaust from the pre-column of the apparatus.

The injection of high volume samples simplifies the preparation method of the sample by reducing or even eliminating the sample-concentration step but causes more complications in the step of separating the solvent from the sample.

In fact is well known, the step that immediately precedes the gas chromatographic analysis with the type of apparatus described above involves the evaporation of a certain quantity of solvent from the solution that constitutes the initially injected sample. Most of the solvent (which is always the most volatile component of the sample) is removed in the vapour phase through the SVE valve. The latter is closed at a certain point in such a way as to transfer the sample compounds and the solvent residue from the pre-column to the capillary analytical column. In other words, what arrives on the capillary analytical column is the remnants of the "desolvation" i.e. what remains after removal of the excess solvent.

The main problem in the known art, especially where the sample volume is high, is to determine the exact moment to close the valve in such a way to give reliable, repeatable analyses and to transfer a quantity of sample to the analytical column compatible with the column itself.

In practice, if the valve is closed too soon, the residual volume arriving on the capillary analytical column will still contain a high percentage of solvent and will overload the analytical column. This results in what is known as the "flooding effect" where the output signal is not sufficiently defined and the efficiency of separation process is prejudiced. By "signal" here is meant the plot generated by detectors of known type downstream of the gas chromatography apparatus. The plot generally consists of a series of peaks, each representing the identification of particular compound contained in the sample.

On the other hand, if the valve is closed too late, some of the components of the sample are eliminated, thus prejudicing the reliability of output signal.

According to the currently known methods, the instant of closing of the valve is determined empirically. In practice, the method for determining the optimal method defined by a series of parameters which correspond to the analysis conditions (i.e. oven temperature, carrier gas pressure, etc.), involves the repetition of single analysis where the solvent evaporation valve opening time is varied in relation to some of the aforementioned parameters. The repetition continues until an output signal is obtained that identifies all the compounds of interest in the sample with the required accuracy.

It is obvious how labourious and expensive such a method of determining optimum analysis conditions is in terms of both resources and time.

The use of gas chromatography analysis apparatus with the method as known at present does not lend itself readily to repeated analysis involving variation of even one of the experimental conditions e.g. the oven temperature in which the analytical capillary column is housed, the initial volume of the sample, the carrier gas pressure or any of the other conditions that influence the previously established opening time of the valve.

OBJECTS OF THE INVENTION

The aim of the present invention is to overcome the drawbacks of the present art.

An object within the scope of this aim is the provision of a device and a method which will produce correct gas chromatographic analyses in a short time and will give well defined signal at the output of the detector.

A further object of the present invention is the provision of a device and a method which will easily reproduce the same experimental conditions for the analysis of different samples, or to repeat the analysis on the same sample while varying one or more of the experimental conditions of a previously determined optimum analytical method.

Another object of the present invention is the provision of a device and a method which will facilitate the analysis of samples having particularly large volumes.

SUMMARY OF THE INVENTION

These objects are achieved by the present invention which relates to a device for the separation into its individual components of a sample which is injected into a stream of carrier gas in the capillary conduit of a gas chromatography analysis apparatus, where the sample consists of a solution of one or more components dissolved in a solvent. The device is characterized by comprising:

means for memorizing a plurality of reference values $R_{evap}$ corresponding to the evaporation rates of solvents, combined with the carrier gases used, corresponding to a plurality of discrete values between respective pre-set intervals, the said discrete values being representative of specific pressure conditions of the carrier gas in the capillary conduit, of specific temperatures to which said capillary column is subjected to, of pre-set initial volumes of the sample injected in said capillary column and of pre-set injection rates of the sample;

means for calculating and memorizing the effective $R_{evap}$ value for evaporation rate of solvent corresponding to actual carrier gas pressures in the capillary conduit, actual temperatures to which the capillary conduits is subjected, actual sample initial volumes and actual injection rate; and means for generating one or more control signals for the gas chromatography analysis apparatus to determine the volumetric fraction of the sample transferred through the capillary conduit in relation to its characteristics and its geometrical dimensions.

The means of calculating and memorizing the $r_{evap}$ and $R_{evap}$ values for the evaporation rates of solvents preferably comprise a processor with a means of function selection and/or data input as well as a means of displaying information related to the said processor.

In fact, the device thus conceived allows the parameters of each phase of solvent separation of the separation to be input and calculated. The processor follows a program which guides the operator through a series of steps to select for example, the carrier gas and/or solvent used, the geometric parameters of the capillary column together with other functions and operations which will be described below.

The invention provides a simple and effective way of controlling the injection of high-volume samples, thus limiting the time spent on preparing the sample for analysis.

It is further possible to memorize the information related to the particular set of conditions for an individual analysis, thus enabling the repetition of the analysis in the same conditions.

The means for generating the control signals for the gas chromatographic analysis apparatus preferably comprise a control unit connected to the processor and the gas chromatographic analysis apparatus.

In this way an "open circuit" control system is set up which has the advantage of allowing the analysis to be done under conditions either controlled automatically by the processor and/or set up manually by the operator. In other words, the operator may select to set up the analysis conditions automatically on the basis of the specific parameters already known (e.g. corresponding to a process of analysis that has already given satisfactory results), but may also choose to change one or more parameters, within determined limits, according to the requirements of the analysis.

The invention also relates to a method for the separation into its individual components of a sample which is injected into a stream of carrier gas in the capillary conduit of a gas chromatography analysis apparatus, in which the sample consists of a solution of one or more components to be analized dissolved in a solvent. The method is characterized by comprising:

the preliminary calculation of a plurality of reference values $R_{evap}$ corresponding to the evaporation rates of solvents, combined with the carrier gas used, corresponding to a plurality of discrete values at respective pre-set intervals, the said discrete values being representative of specific pressure conditions of the carrier gas in the capillary conduit of specific temperatures to which said capillary conduit is subjected to, of pre-set initial volumes of the sample injected in said capillary conduit and pre-set injection rates of the sample;

the calculation of the effective $R_{evap}$ value for evaporation rate of solvent corresponding to actual carrier gas pressures in the capillary column, actual temperatures to which the capillary column is subjected to, actual sample initial volumes and actual injection rates;

the generation of one or more control signals for the gas chromatography analysis apparatus to determine the volumetric fraction of the sample transferred through the capillary conduit in relation to its characteristics and its geometrical dimensions.

In practice, it is particularly advantageous to establish beforehand the volumetric fraction of the sample that is to go onto the analytical capillary column. The relation which expresses the volumetric equilibrium for a sample injected onto a gas chromatography analysis apparatus is the following:

$$V_{inj}=V_{evap}+V_{ret} \tag{I}$$

where:

$V_{inj}$ is the total volume of the sample injected, i.e. the sum of the volume of the solvent and the volume of the compounds to be analyzed;

$V_{evap}$ is the fraction of the volume which is removed through the SVE valve, the said volume fraction being comprised of solvent alone, and $V_{ret}$ is the fraction of the volume that is retained on the pre-column, the said volume fraction being comprised of compounds to be analyzed and the residual percentage of solvent. This is in practice the quantity of sample which will reach the analytical capillary column when the SVE valve is closed.

Since the volume injected $V_{inj}$ and the volume which goes onto the capillary column $V_{ret}$ are known, then the volume of solvent vented through the SVE valve $V_{evap}$ can be calculated from equation (I).

When $V_{evap}$ is known, the valve open time t is given by the relation $$t=V_{evap}/r_{evap} \tag{II}$$

in which $r_{evap}$ is the evaporation rate of the solvent under operating conditions.

However, calculating the evaporation rate $r_{evap}$ of the solvent is not simple, since the value is influenced by many factors which depend on, for example, the physical characteristics of the liquid and vapour phases of the solvent, the physical characteristics of the carrier gas, the conditions in which the solvent is separated i.e. the initial temperature of the injected sample, the volume initially injected, the injection rate, the carrier gas pressure and the oven temperature. Further factors influencing the evaporation rate is the nature of the inner surface of the pre-column and its physical parameters i.e. length and internal diameter.

In practice, by using a pre-column with fixed physical parameters, the following relationship can be established for the $r_{evap}$:

$$r_{evap}=f(P,T,V_{inj},U_{inj},\text{Solv}) \tag{III}$$

where the variables P, T, $V_{inj}$, are respectively the carrier gas pressure in the column, the oven temperature, and the volume injected, i.e. the analysis initial conditions which are maintained constant during injection and removal of the solvent. The variable $U_{inj}$ is the sample injection rate, while Solv represents the set of those variables related to the physical characteristics of the solvent e.g. density, viscosity, entropy of the liquid and vapour states, the specific heat in the liquid state etc.

To avoid having to calculate an extremely complex equation, which would take a lot of time even on powerful computers, it is preferred to determine a series of only evaporation rate reference values $R_{evap}$ empirically for pre-set values of the variables P, T, $V_{inj}$, $U_{inj}$.

The experimental determination of a series of evaporation rate reference values $R_{evap}$ for pre-set values of the four variables P, T, $V_{inj}$, $U_{inj}$ also avoids the difficulty of defining the numerous Solv variables that define the solvent, together with those which characterize the gaseous mixture composed of solvent in the vapour phase and the carrier gas.

In practice, for each combination of one of a number of solvents with one of a number of carrier gases, a reference value $R_{evap(i,j,k,s)}$ is determined experimentally for the evaporation rate of the solvent for a plurality of values of only the variables $P_i, T_j, V_k$ and $U_s$ within pre-set limits. The values $R_{evap(i,j,k,s)}$ for a determined combination of solvent/ carrier gas can be collected into a single matrix and easily memorized in a computer.

According to a preferred aspect of the method proposed by the present invention, the effective evaporation rate $r_{evap}$ is calculated by interpolation of the geometrically nearest $R_{evap}$ reference values in the environment determined by the actual conditions of carrier gas pressure in the capillary conduit, actual temperature, to which is subject the capillary conduit, the actual initial sample injected volume and the actual sample injection rate.

This allows considerable simplification of the calculation of the effective evaporation rate of the solvent for any set of values of the variables P, T, $V_{inj}$ and $U_{inj}$ imposed in the respective ranges of variability.

The method also allows conditions for the carrying out of the analysis to be optimized for all its phases.

For example, the method provides for the calculation of the temperature and pressure conditions which must be maintained during sample injection and solvent removal to ensure the maximum volume of injected sample in the pre-column, and the distinct temperature and pressure conditions which must be maintained after the SVE valve is closed to ensure optimum flow in the analytical capillary column.

As a further optimization possibility, the method provides for the calculation of the carrier pressure and temperature that must be maintained during the sample injection and solvent removal phase in order to ensure a pre-set flow rate of solvent vapour through the SVE valve, and the distinct temperature and pressure conditions which must be maintained after the SVE valve is closed to ensure optimum flow in the analytical capillary column.

Provision is also made for the calculation and/or manual setting of carrier gas pressure and temperature that must be maintained constant during the entire analysis i.e. not only for the sample injection and solvent removal phase but also for the transfer of the compounds of the sample residue from the pre-column to the capillary column after the SVE valve is closed.

These and other advantages will be more evident from the description which follows, which is illustrative and not limiting, where reference is made to the attached sketches in which:

BRIEF DESCRIPTION OF THE DRAWINGS

FIG. 2 shows the operations carried out or made available by the computer according to an embodiment of the method of the present invention;

DESCRIPTION OF THE PREFERRED EMBODIMENTS

Figure 1:
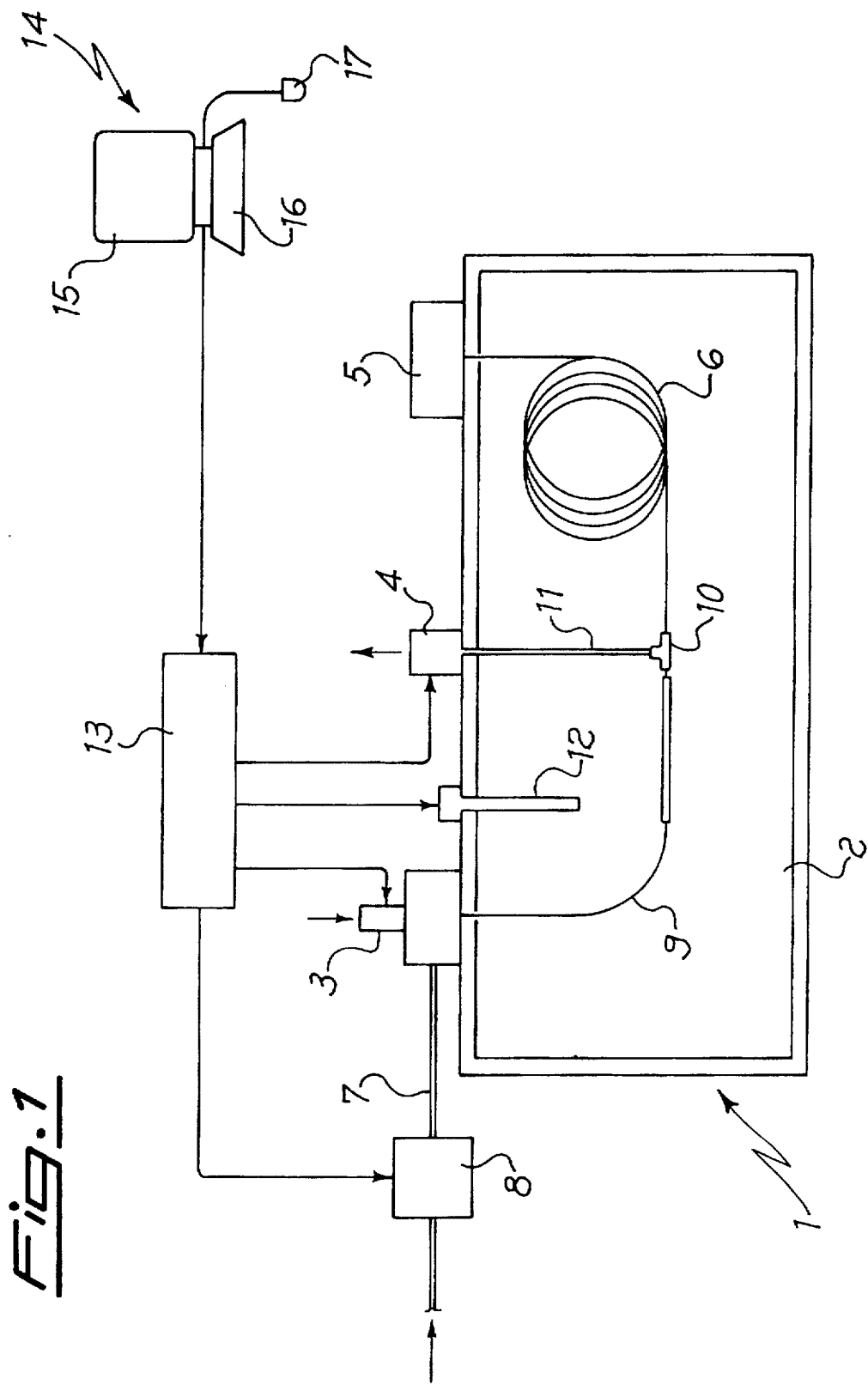
FIG. 1 is a scheme of the device according to the invention.

The apparatus 1 comprises substantially an oven 2, an injector 3 (preferably of the "on-column" type) to inject the sample to be analyzed, a valve 4 to allow the evacuation of the solvent in the vapour phase (SVE valve), a detector 5 connected to the outlet of the capillary analytical column 6, lodged in the oven 2. To the injector 3 is connected a supply line 7 for the carrier gas; on the said supply line a valve 8 is arranged, said valve being operated electronically to regulate the flow rate and the pressure of the carrier gas to the apparatus 1.

Inside the oven 2, as well as the capillary column 6, there is a pre-column 9 connected downstream of the injector 3 and upstream of the capillary analytical column 6. Between the pre-column tube 9 and the analytical capillary column 6 there is a "T" junction 10 from which a tube 11 departs that connects the capillary ducts 6 and 9 to the valve 4. Inside the oven 2 there are means 12 of regulation of the temperature in the same oven.

The device according to the invention provides for a control unit 13 to generate the necessary control signals for the valve 8 on the carrier gas supply line, the means 12 of regulating the temperature, the injector 3 and the evacuation valve 4 of the solvent.

The control unit 13 is in turn connected to a computer 14 from which it receives the inserted and/or calculated data for each phase of analysis. The computer 14 may be of any commonly known type, comprising at least a monitor 15, a hard-disk memory unit, a RAM memory, a keyboard 16 and a mouse 17 to select functions and/or insert data.

The hard-disk of the computer 14 stores a plurality of reference values $R_{evap}$ corresponding to the evaporation rates of the solvent in relation to a corresponding plurality of discrete values of the variables $P_i$, $T_j$, $V_k$ and $U_s$ within respective pre-set intervals. The values of $R_{evap(i,j,k,s)}$ for a particular combination of carrier gas and solvent can be collected into a single matrix and memorized on the computer 14 as such.

In other words, the reference values of the evaporation rates of the solvent are calculated only in terms of pre-set conditions i.e. for discrete representative values of the carrier gas pressure in the supply line 7, of the temperature inside the oven 2, of the initial volume of injected sample, and of the injection rate.

The keyboard 16 and the mouse 17 allow the insertion or the selection of the data which characterize the actual analysis in all its phases.

Also memorized in the computer are the data relating to the geometrical parameters of the capillary columns 6 and 9, e.g. length and internal diameter of the capillary column 6, data related to the volume of the injected sample, and data relating to the temperature inside the oven 2 and the pressure conditions of the carrier gas. All data are arranged in configurations which allows it to be moved easily between the hard-disk and the RAM.

The computer 14 allows the effective value of the evaporation rate $r_{evap}$ of the solvent in use to be calculated in relation to data stored in the memory and/or inserted by the operator, and thus to calculate the parameters which characterize each phase of the gas chromatography analysis.

FIG. 2 shows a sequence comprising some of the steps the operator must go through on the computer 14 to set up an analysis correctly. In the case shown, it is presumed that some parameters are pre-inserted e.g. those related to the kind of carrier gas to be used and the type of retention gap 9 used in the gas chromatography apparatus. Furthermore, the reference values $R_{evap}$ are presumed to have been already calculated and memorized on the computer 14.

According to a preferential embodiement of the invention, a program is used which allows interaction between the operator and the computer 14 by means of a graphic interface. The selection of the data to be input in the steps of FIG. 2 referred to above can be done either by the keyboard 16 or the mouse 17. It is important to state that the program run by the computer 14 has other functions which are not shown in FIG. 2; e.g. the memorization of a particular configuration on the hard disk; the retrieval of a particular configuration from the hard disk and recally it to the RAM; the sending of information related to a particular configuration to the control unit 13.

The information contained in blocks 201 and 202 is requested at step 20 of FIG. 2.

Block 201 indicates the selection of the solvent used in the preparation of the sample to be analyzed. The selection of the solvent gives the computer 14 the information it needs to identify the matrix of reference values $R_{evap}$ to be used to calculate the actual values $r_{evap}$ related to the evaporation rate of the solvent.

Block 202 indicates the inputting of the geometrical characteristics of the analytical capillary column, in particular the length and internal diameter, i.e. the data which influence the flow in the analytical column 6 after the solvent elimination phase.

The order in which operations 201 and 202 are carried out at stage 20 is unimportant.

The information contained in blocks 211 and 212 is requested at step 21 of FIG. 2. Blocks 211 and 212 indicate respectively the carrier gas pressure and the oven temperature at which the capillary conduit sections 6 and 9 in the oven 2 are maintained during the desolvation. Once it has received the values of pressure and temperature, the computer 14 proceeds to calculate the series of parameters particularly important indicated by the block 213. In particularly, it is made the calculation of the actual evaporation rate $r_{evap}$ of the solvent. Once $r_{evap}$ is known, the maximum injection volume $V_{max}$, the volume of pre-column 9 with the valve 4 open and the volume of the conduit comprising the analytical column 6 and the pre-column 9 with the valve 4 closed, can all be determined.

At stage 22 information (block 221) relating to injected sample volume is requested, while at stage 23 information (block 231) relating to residual volume which remains in the pre-column 9 after the valve 4 has been closed and which will transfer to the analytical column 6 after the valve 4 has been closed, is requested.

At this point, the computer 14 can complete the calculation of the other remaining parameters needed to complete the information necessary to the carrying out of the analysis.

Block 232 contains the information relating to the sample injection rate and the time the valve 4 remains open after the end of the sample injection phase.

Figure 4:
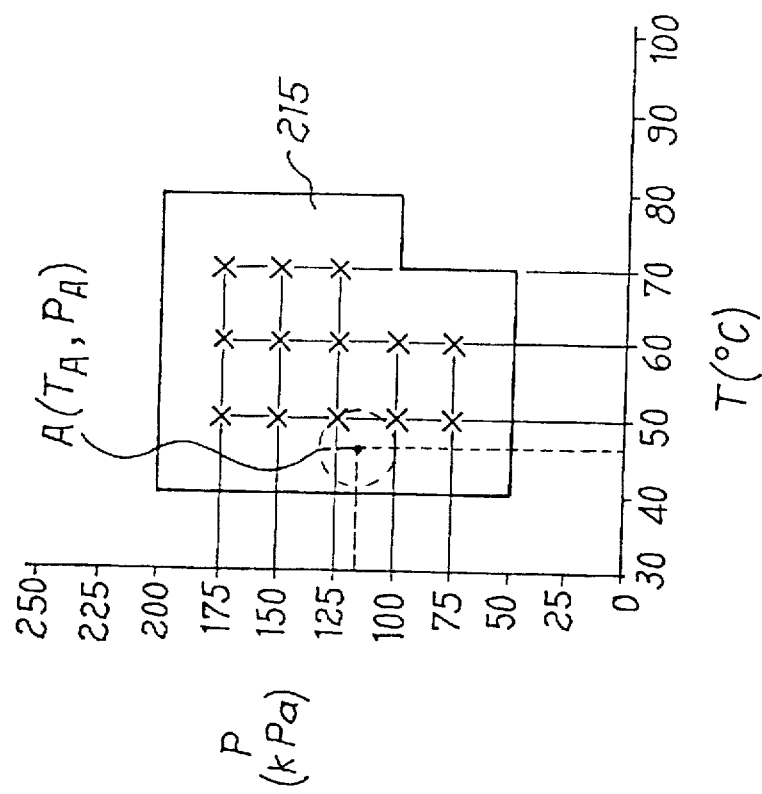
FIG. 4 is a diagram of the reference values $R_{evap}$ on the domain shown in FIG. 3 of the Cartesian plane (T;P).
Figure 3:
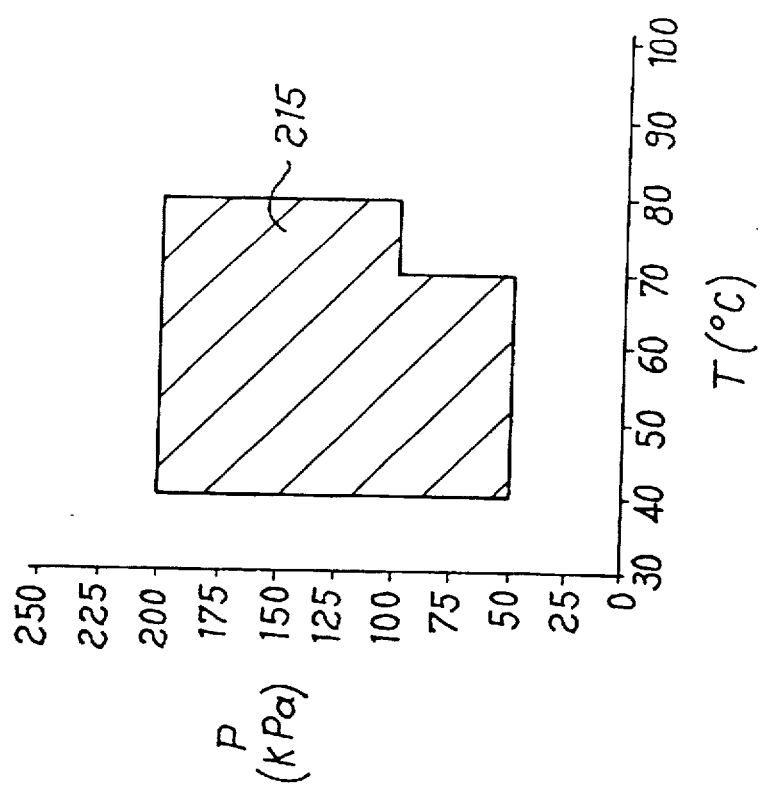
FIG. 3 is a diagram of the domain of selectable gas pressures and oven temperatures on the Cartesian plane (T;P).

FIG. 3 shows a Cartesian plane (T,P) containing the domain 215 from which the values of P and T can be selected at stage 21 of FIG. 2. FIG. 4 shows the same domain 215 of FIG. 3 in which the reference values $R_{evap}$ calculated corresponding to the discrete value pairs $(P_i, T_j)$ are indicated by (x).

The point $A(T_A, P_A)$ is any point within the domain 215 for which there is no a priori reference value $R_{evap}$; i.e. a pair of values $T_A$ and $P_A$ which represent the conditions of temperature and pressure imposed by the operator in stage 21 of FIG. 2.

According to the method of the present invention, the calculation of the actual value of the evaporation rate of the solvent $r_{evap}$ is by interpolation to the geometrically nearest reference value $R_{evap}$ to the point A i.e. the $R_{evap}$ for which the expression $$(P_A-P_i)^2+(T_A-T_j)^2$$

is minimum.

For example, the geometrically nearest reference value $R_{evap}$ to point A in FIG. 4 is that corresponding to T=50° C. and P=125 kPa.

Figure 5:
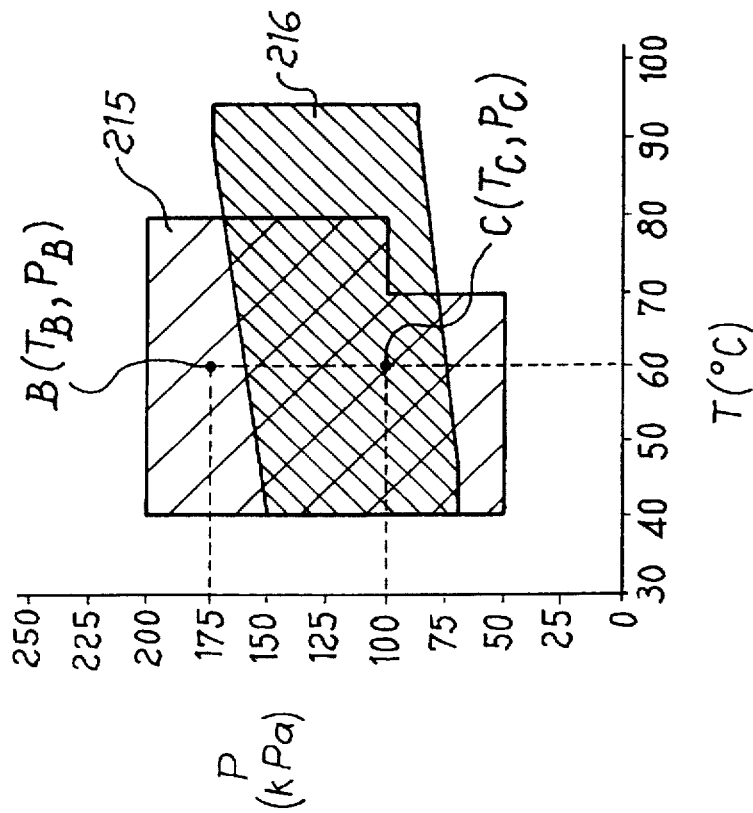
FIGS. 5 to 8 show diagrams of some examples of Cartesian planes (T;P) similar to those displayed on the computer monitor during the inserting of gas pressures and oven temperatures values according to the method of the present invention.

FIG. 5 shows an example of a Cartesian plane (T,P) which is displayed on the monitor 15 of the computer 14 during selection of the temperature and pressure by the operator, during the initial selection of such values. The hatched area 215 in FIG. 5 shows the domain 215 already indicated in FIGS. 3 and 4, while the shaded area 216 shows the domain of the values of temperature and pressure which would give optimum flow conditions in the capillary column 6 after the valve 4 is closed.

In practice, the point D $(T_D, P_D)$ could be in any position inside the area 215 but is not limited in any way to any position in area 216. So, if point D is inside the intersection of the areas 215 and 216 (as is shown in FIG. 5), then conditions can be chosen which are valid both for the sample injection and solvent removal phase, and for the transfer of the residual sample fraction from the pre-column 9 to the analytical capillary column 6. If point D is inside the area 215 but not inside area 216, then the flow rate through the column 6 will not be optimum for the analytical capillary column size after the valve 4 is closed.

According to an advantageous aspect of the present invention, once a desired temperature has been selected, it is possible to select an initial pressure suitable to the sample injection and solvent removal phase, and a second pressure suitable for the sample transfer to the analytical column phase.

Figure 6:
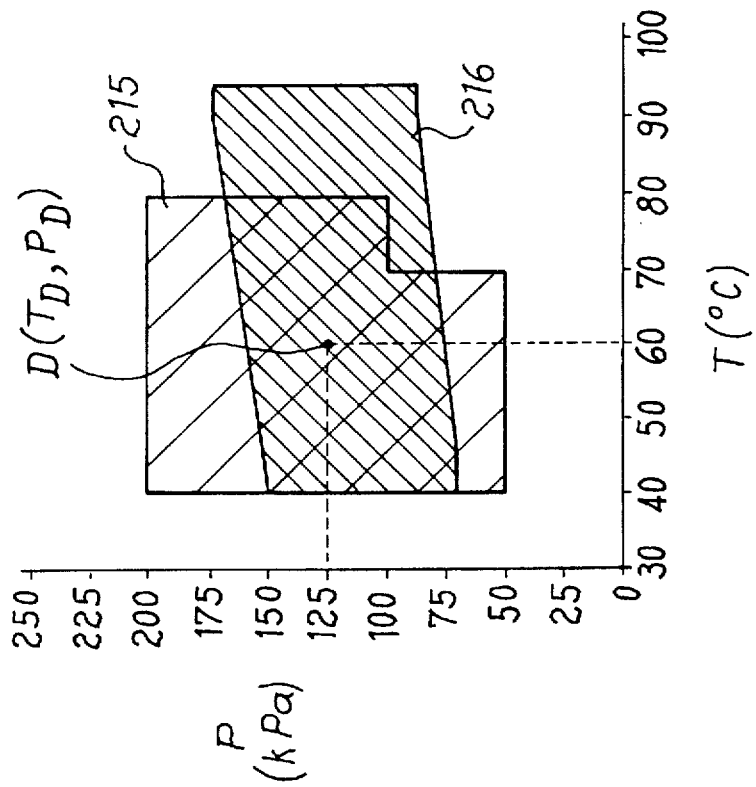

As is shown in FIG. 6, an initial point B $(T_B, P_B)$ can be selected which defines the temperature and pressure conditions during injection of the sample and removal of the solvent, and a second point C $(T_C, P_C)$ which defines the temperature and pressure conditions after the valve 4 is closed. Point B may be anywhere within the area 215 and point C may be anywhere within the area 216.

Both points B and C define preferably identical temperatures of the oven 2 that is $(T_B=T_C)$ while the carrier gas pressures may be different in successive phases. In this way it is possible to optimize each phase of the analysis according to different criteria.

For example, an initial criterium for optimization might be maximum volume injectable in the pre-column 9. It is known that—all other things (e.g. temperature and pre-column type) being equal—the volume of sample which can be injected on the pre-column increases with increasing carrier gas pressure. However, a high carrier gas pressure may not be ideal in the capillary analytical column after the SVE is closed. So, it is particularly advantageous to be able to set one pressure $P_B$ to give large volume sample injection and then a second pressure $P_C$ which gives optimum analytical column flow performance. The program run by the computer 14 facilitates the selection of such optimization which may be selected at stage 21 of FIG. 2. In particular, a diagram similar to that of FIG. 5 is shown on the monitor 15 when the operator must select temperature and pressure, on which the point D represents the predefined values of temperature $T_D$ and pressure $P_D$, e.g. the default values calculated by the program and/or memorized by the computer 14. The operator may keep those values or adjust the temperature and/or pressure while keeping the point D within the area 215.

By selecting the optimization option (e.g. based on the maximum volume of sample that could be injected), the monitor displays the diagram according to FIG. 6 where for the predefined temperature $T_D$ (with $T_D=T_B=T_C$) a pressure value B is chosen, calculated automatically by the program, which gives the maximum volume of sample that may be injected, while the pressure value C is chosen, again calculated automatically by the program, which gives the optimum flow conditions in the analytical capillary column. In this case the pressure PB is always greater than the pressure PC while the temperature TB and TC are kept constant at the same value TD which was calculated or set before the optimization.

Even in the case shown in FIG. 6, the operator can adjust the position of point B inside the area 215 and the position of point C within the area 216. It must be remembered that any adjustment of point B and/or point C will alter the optimum conditions that were previously calculated by the program for the temperature TD previously calculated or set.

A further criterion of optimization of the method according to the present invention is the imposition of a pre-set solvent flow-rate through the valve 4. This option (which is particularly practical for operators in the field) allows the automatic calculation of conditions which give optimum flow rate in the analytical capillary column after the valve 4 is closed, while the solvent flow-rate through the said valve 4 in the prior phase is set by the operator. The practice is widespread of estimating approximately both the length of time the valve SVE is open and the quantity of solvent removed through it on the basis of the flow-rate through the same valve. In practice, starting from the temperature $T_D$ previously calculated or set (FIG. 5) and selecting the optimization option, it is- requested the imputting of the corresponding value to the desired flow-rate through the SVE valve. After this setting has taken place, a diagram is shown on the monitor as in FIG. 6 with two points B and C. In this case, however, the point B corresponds to the temperature $T_B$ and pressure $P_B$ which give the required SVE valve flow-rate, while the point C corresponds to the temperature $T_C$ and pressure $P_C$ which give the optimum flow-rate conditions in the analytical capillary column. In this case, unlike that of the optimization for the maximum injectable sample volume, the point B may be below point C. The possibility of establishing different conditions of pressure $P_B$ and $P_C$ during the analysis method, together with the optimization of such conditions according to any required criterion, may prove useful, if not indispensable, for working in particular circumstances. An example of such conditions is shown in FIGS. 7 and 8, in which the areas 215 and 216 have very limited overlapping portions.

Figure 7:
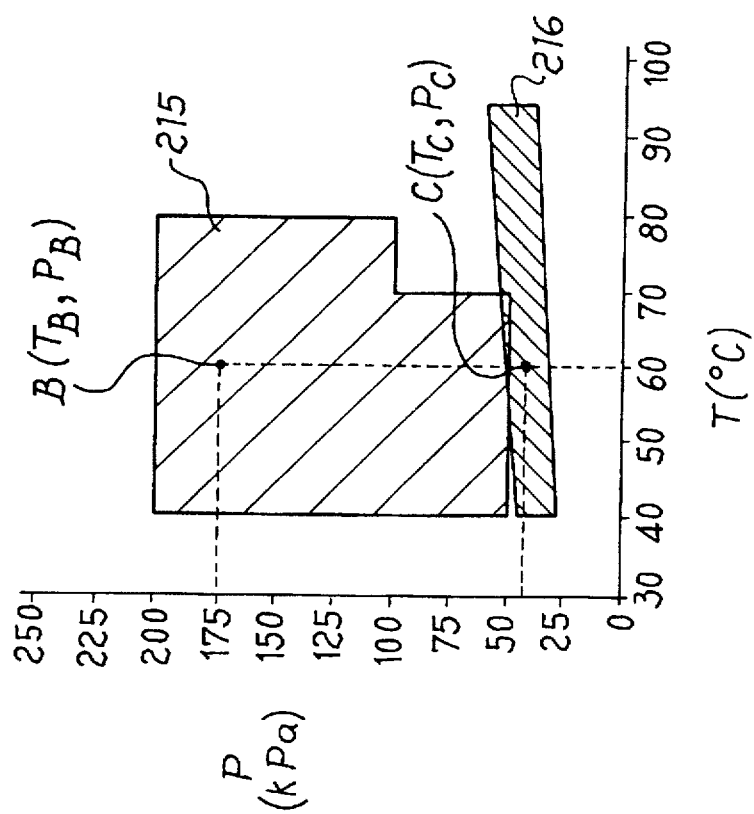
Figure 8:
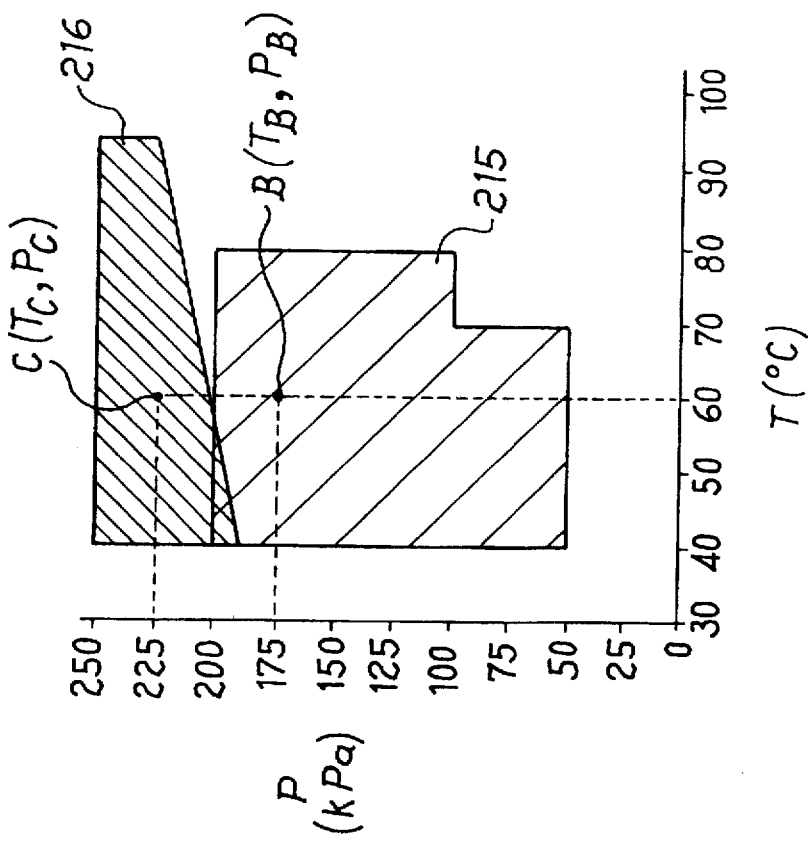

The case in FIG. 7 is a real situation in which the solvent is n-hexane, the analytical capillary column is 13 meters long with an internal diameter of 0.1 mm. In the case in FIG. 8 the solvent is n-hexane, but the analytical capillary column is 5 meters long with an internal diameter of 0.32 mm.

The ability to select different conditions of temperature and/or pressure before and after the closing of the SVE valve allow the operator to select the most favourable conditions in which to carry out the analysis.

In any case, provision has been made to adjust other variables in order to correct the values that have been calculated automatically by the program. In particular, the program provides for the manual adjustment of certain parameters, among which are the sample injection flow-rate, the opening time of the valve 4, at least the carrier gas pressure during the sample injection and solvent removal phases, together with a temperature value different to that previously set or calculated by the program.

Any optimization previously carried out automatically by the program cannot be guaranteed after the variation of the aforementioned parameters by the operator. However, the ability to vary such values may be useful in the case of variation in some of the characteristics of solvents and/or carrier gases (e.g. purity) which are nominally similar but originate from different suppliers.

We claim:

1. Method for the separation into its individual components of a sample which is injected into a stream of carrier gas in a capillary conduit of a gas chromatography analysis apparatus, said sample consisting of a solution of one or more components to be analyzed, dissolved in a solvent, the method being characterized by comprising:

calculating a plurality of $R_{evap}$ reference values corresponding to the evaporation rates of said solvent, combined with the carrier gases used, corresponding to a plurality of discrete values at respective pre-set intervals, said discrete values being representative of specific pressure conditions of the carrier gas in said capillary conduit of specific temperatures to which said capillary conduit is subjected to, of pre-set initial volumes of the sample injected in said capillary conduit and pre-set injection rates of the sample;

calculating the effective $r_{evap}$ value for evaporation rates of solvents corresponding to actual carrier gas pressures in the capillary conduit, actual temperatures to which is subjected said capillary conduit, actual initial volumes of injected sample and actual injection rates of said sample;

generating at least one control signals for the gas chromatography analysis apparatus to determine the volumetric fraction of the sample transferred through the capillary conduit in relation to its characteristics and its geometrical dimensions.

2. Method according to claim 1, characterized by the effective evaporation rate $r_{evap}$ being calculated by interpolation to the geometrically nearest $R_{evap}$ reference values in a set of values representative of the actual conditions of carrier gas pressure in said capillary conduit, the actual temperatures to which the capillary conduit is subject, the actual sample volume initially injected and the actual injection rate of said sample.

3. Method according to claim 1, characterized by the capillary conduit comprising a pre-column and an analytical capillary column of the apparatus for gas chromatography analysis, and by comprising fitting a valve means downstream of the pre-column and upstream of the analytical capillary column for the removal of the solvent vapour evaporated from the sample.

4. Method according to claim 3, characterized by calculating a maximum volume of sample that could be injected onto the pre-column.

5. Method according to claim 3, characterized by calculating a volumetric fraction of the sample removed by evaporation through the valve means in relation to the quantity of sample which is transferred to the analytical capillary column of the gas chromatography analysis apparatus.

6. Method according to claim 3, characterized by calculating an interval of time corresponding to the duration of the solvent removal phase during the period in which the valve means remains open, the beginning of the open period coinciding with the ending of the phase of sample injection on the pre-column.

7. Method according to claim 3, characterized by the phase of sample injection on the pre-column and the phase of solvent removal through the valve means being carried out while maintaining the pre-column at the same temperature and the carrier gas at the same pressure.

8. Method according to claim 1, characterized by calculating an initial value corresponding to the conditions of carrier gas pressure in the capillary conduit for a specific temperature during the phase of sample injection in the pre-column and during the removal of evaporated solvent through the valve means, said initial pressure value being calculated to ensure the maximum volume of sample that can be injected onto the pre-column.

9. Method according to claim 1, characterized by calculating an initial value corresponding to the conditions of carrier gas pressure in the capillary conduit for a specific temperature during the phase of sample injection on the pre-column and during the removal of evaporated solvent through the valve means, said initial value being calculated to ensure a pre-set flow-rate through the valve means in relation to the characteristics and geometrical dimensions of the pre-column.

10. Method according to claim 1, characterized by calculating a second value corresponding to the conditions of carrier gas pressure in the pre-column and in the analytical capillary column after the closure of the valve means, the second value being calculated to ensure a pre-set flow-rate through the analytical capillary column in relation to its characteristics and geometrical dimensions.

11. Method according to claim 10, characterized by the temperature with which the initial pressure is calculated being the same temperature with which the second pressure value is calculated.

12. Device for the separation into its individual components of a sample which is injected into a stream of carrier gas in a capillary conduit of a gas chromatography analysis apparatus, in which the sample consists of a solution of one or more components to be analyzed dissolved in a solvent, the device is characterized by comprising:

means for calculating and memorizing a plurality of reference values $R_{evap}$ corresponding to the evaporation rate of said solvent, combined with said carrier gas, corresponding to a plurality of discrete values between respective pre-set intervals, the discrete values being representative of specific pressure conditions of the carrier gas in said capillary conduit, of specific temperatures to which said capillary conduit is subjected to, of pre-set initial volumes of the sample injected in said capillary conduit and pre-set injection rate of said sample;

means for calculating and memorizing the $r_{evap}$ effective value for evaporation rate of solvent corresponding to actual carrier gas pressures in said capillary conduit, of specific temperatures to which said capillary conduit is subjected to, for actual injected sample initial volumes and for actual injection rate; and means or generating one or more control signals for the gas chromatography analysis apparatus to determine the volumetric fraction of the sample transferred through the capillary conduit in relation to its characteristics and its geometrical dimensions.

13. Device according to claim 12, characterized by the means for calculating and memorizing the $R_{evap}$ and $r_{evap}$ values for the evaporation rate of solvent comprising at least one computer.

14. Device according to the claim 13, characterized by said means for generating said control signals comprising a control unit that is connected to said computer and said gas chromatography analysis apparatus.

15. Device according to claim 12, characterized by said capillary conduit comprising a pre-column of said apparatus for gas chromatography analysis.

16. Device according to claim 12, characterized by said capillary conduit comprising an analytical capillary column of said apparatus for gas chromatography analysis.

17. Device according to claim 12, characterized by said apparatus for gas chromatography analysis comprising an analytical capillary column lodged in an oven, an injector fitted upstream of said analytical capillary column, a supply line for the carrier gas connected to said injector, a pre-column lodged in said oven between said injector and the analytical capillary column, valve means fitted downstream of the pre-column and upstream of the analytical capillary column for the removal of the solvent vapour from the apparatus, means of regulating the temperature of said oven, and means of regulating the pressure of said carrier gas.

18. Device according to claim 17, characterized by said control unit comprising a means of generating at least one control signal for said injector, at least one control signal for said valve means, at least one control signal for said means of regulating oven temperature, at least one control signal for said means of regulating the pressure of said carrier gas in said capillary conduit.

* * * * *